United States Patent [19]
Yamashita

[11] 4,195,904
[45] Apr. 1, 1980

[54] OPTICAL SYSTEM OF VIEWING-DIRECTION CHANGING ATTACHMENT FOR ENDOSCOPES

[75] Inventor: Nobuo Yamashita, Tama, Japan

[73] Assignee: Olympus Optical Co., Ltd., Tokyo, Japan

[21] Appl. No.: 867,498

[22] Filed: Jan. 6, 1978

[30] Foreign Application Priority Data

Jan. 18, 1977 [JP] Japan .................................... 52-4095

[51] Int. Cl.² ............................................ G02B 23/02
[52] U.S. Cl. ...................................... 350/68; 350/25; 350/54; 350/286
[58] Field of Search ...................... 350/25, 45, 54, 68, 350/96.26, 235, 91, 286

[56] References Cited

U.S. PATENT DOCUMENTS

| | | | |
|---|---|---|---|
| 3,005,452 | 10/1961 | Pitman | 350/25 X |
| 3,818,902 | 6/1974 | Kinoshita et al. | 350/96.26 X |

Primary Examiner—John K. Corbin
Assistant Examiner—Matthew W. Koren
Attorney, Agent, or Firm—Cushman, Darby & Cushman

[57] ABSTRACT

An optical system of viewing-direction changing attachment for endoscopes comprising a first reflecting means having a reflecting surface for changing the observing direction and a second reflecting means having a reflecting surface for changing the illuminating direction and arranged so that the reflecting surface for changing the illuminating direction comes to a fore position compared with the reflecting surface for changing the observing direction in order to enable to illuminate and observe a wide area being free from ghost image and flare.

4 Claims, 7 Drawing Figures

OPTICAL SYSTEM OF VIEWING-DIRECTION CHANGING ATTACHMENT FOR ENDOSCOPES

BACKGROUND OF THE INVENTION (a) Field of the Invention

The present invention relates to an optical system of viewing-direction changing attachment for endoscopes and, more particularly, to an optical system of viewing-direction changing attachment to be attached to a distal end of a flexible or inflexible endoscope of forward-viewing type in order to change the observing and illuminating directions by about 90° so that the endoscope is used also for side viewing.

(b) Description of the Prior Art

To use an endoscope of forward-viewing type for side viewing, a mirror may be arranged at its distal end as shown in FIG. 1. In FIG. 1 which shows a distal end of an endoscope, numeral 1 designates the endoscope, numeral 2 designates an image guide and numeral 3 designates an objective arranged at the end of the image guide 2. The image guide 2 and objective 3 constitute an observing optical system. Numeral 4 designates a light guide which is arranged in parallel with the image guide 2 and constitute an illuminating optical system. By this endoscope, an object in forward-viewing direction of the endoscope 1 is illuminated by the light guide 4 and is observed by the objective 3 and image guide 2. When a mirror 5 is arranged at the distal end of the above-mentioned endoscope of forward-viewing type by inclining the mirror 5 by about 45° in respect to the forward-viewing direction, it is possible to observe an object in side-viewing direction by illuminating it by the illuminating light from the light guide.

However, in case of side viewing by using an endoscope of forward-viewing type according to the above-mentioned method, a part of illuminating light from the light guide 4 will directly enter the objective 2 as it is evident from FIG. 1 and will cause considerable ghost and flare. Moreover, as the end portion of the endoscope 1 partially eclipses the illuminating light, it becomes impossible to effectively illuminate a wide area and this is considerably inconvenient in practical use.

SUMMARY OF THE INVENTION

It is, therefore, a primary object of the present invention to provide an optical system of viewing-direction changing attachment for endoscopes to be attached to the distal end of an endoscope and comprising a first reflecting means arranged in front of the observing optical system of the endoscope and a second reflecting means arranged in front of the illuminating optical system of the endoscope, the optical system of viewing-direction changing attachment enabling to illuminate and observe a wide area without causing ghost or flare by illuminating light.

DETAILED DESCRIPTION OF THE PREFERRED EMBODIMENTS

Figure 2:
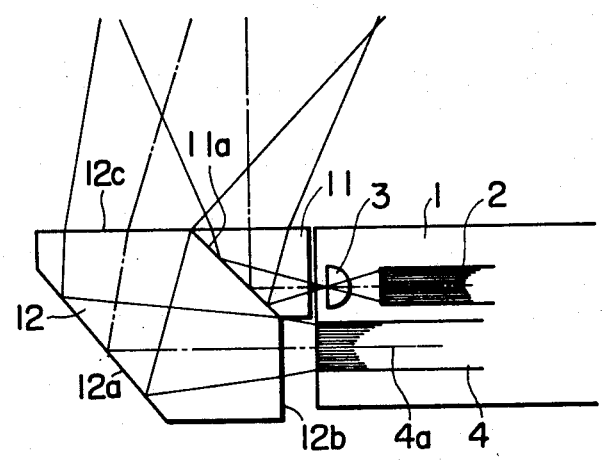
FIG. 2 shows a schematic view illustrating a first embodiment of the optical system according to the present invention.

In the following, the optical system of viewing-direction changing attachment for endoscopes according to the present invention is described in detail referring to the embodiments shown on the accompanying drawings. In FIG. 2 showing the first embodiment of the present invention, numeral 11 designates a first prism for changing the viewing direction of the observing optical system. The surface 11a of the prism 11 is arranged as a mirror surface and serves as the reflecting surface for changing the viewing direction. Numeral 12 designates a second prism for changing the illuminating direction of the illuminating optical system. The surface 12a of the prism 12 serves as the reflecting surface for changing the illuminating direction. The optical system according to the present invention comprises the above-mentioned prisms 11 and 12 which are integrally fixed to each other directly or through a light-shielding plate so that an attachment is formed. When the above-mentioned optical system is attached to the distal end of the endoscope 1 as shown in FIG. 2, the illuminating light from the light guide 4 is reflected by the surface 12a of the prism 12 and illuminates an object in the side-viewing direction of the endoscope.

The light from the object illuminated by the illuminating light is reflected by the mirror surface 11a of the prism 11 and is transmitted to the observer's side through the objective 3 and image guide 2.

Figure 1:
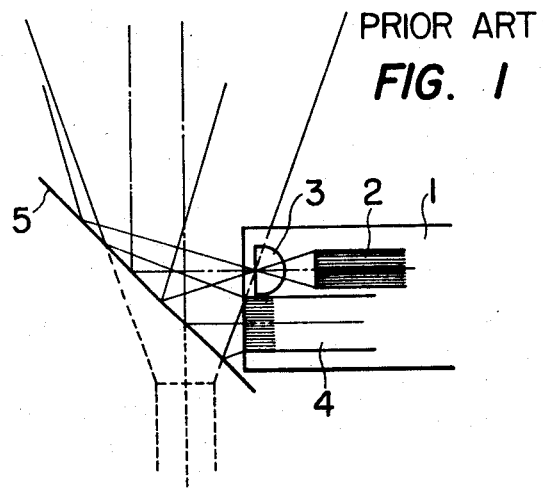
FIG. 1 shows a schematic view showing a known optical system for using an endoscope of forward-viewing type for side viewing.

When the above-mentioned optical system is used, the illuminating light from the light guide does not enter the objective and, therefore, flare or ghost does not occur. Besides, as the illuminating light is not eclipsed by the end portion of endoscope or the like, it is possible to illuminate a wide area. Moreover, as it is possible to make the equivalent optical path length from the end face of the light guide 4 to the exit surface 12c of the prism 12 approximately equal to the optical path length in the optical system in which a reflecting mirror is used as shown in FIG. 1, it is possible to make the illuminating area wide even when the reflecting surface 12a and exit surface 12c are not made large.

Furthermore, as it is not necessary to make the reflecting surface 12a of the prism 12 parallel with the mirror surface 11a of the prism 11, it is possible to shift the illuminating area toward the field of the observing optical system by arranging the reflecting surface 12a of the prism 12 at a large angle in respect to the axis 4a of the light guide 4. Therefore, it is possible to eliminate parallax to be caused by the distance between the optical axes of the observing optical system and illuminating optical system. Consequently, it is possible to make the field angle of the observing optical system still larger.

Figure 3:
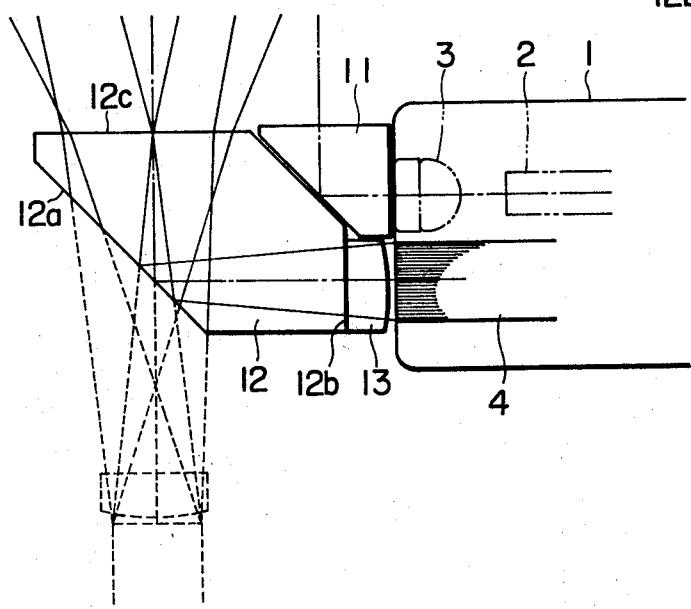
FIG. 3 shows a schematic view illustrating a second embodiment of the optical system according to the present invention.
Figure 4A:
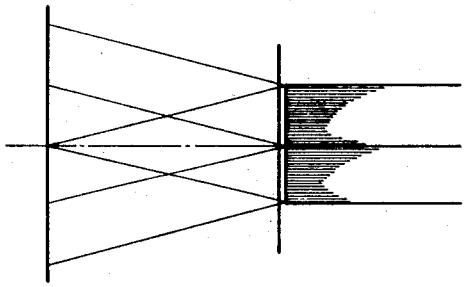
FIGS. 4A and 4B respectively show states of divergence of light by the first and second embodiments.
Figure 4B:
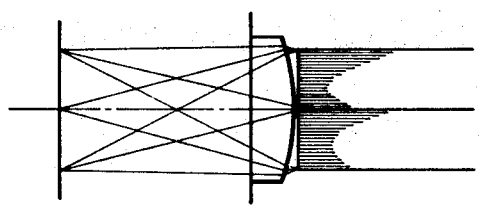
Figure 5B:
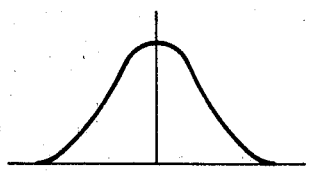
FIGS. 5A and 5B respectively show graphs illustrating distribution curves of illuminating light intensity in respect to illuminating angles in cases of the first and second embodiments.
Figure 5A:
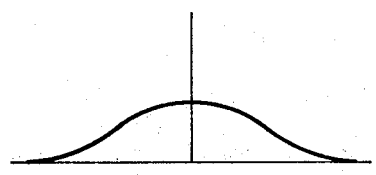

FIG. 3 shows a second embodiment of the optical system according to the present invention. In the optical system according to the second embodiment, a positive lens 13 is arranged adjacent to the surface 12b of the second prism 12 through which the illuminating light from the light guide enters the prism 12. When arranged as above, principal rays (rays which come out straight from optical fibers in the light guide) are inclined toward the optical axis and, therefore, it is possible to prevent divergence of illuminating light. In case of the second embodiment, it is therefore possible to further reduce eclipse of illuminating light compared with the first embodiment shown in FIG. 2. FIG. 4A shows the state of divergence of illuminating light in case of the first embodiment shown in FIG. 2 and FIG. 4B shows the state of divergence of illuminating light in case of the second embodiment shown in FIG. 3. Besides, FIG. 5A shows a distribution curve of illuminating light intensity in respect to the illuminating angles in case of the first embodiment and FIG. 5B shows a distribution curve of illuminating light intensity in respect to the illuminating angles in case of the second embodiment. When the positive lens is used as shown in FIG. 3, principal rays are inclined toward the optical axis so that a wide area is illuminated and, at the same time, the distribution characteristic of light intensity also becomes more favourable as shown in FIG. 5B compared with the distribution characteristic of light intensity of the first embodiment shown in FIG. 5A. In case of the second embodiment, it is possible to obtain uniform illumination for a wide area as explained in the above and, therefore, it is also possible to substantially eliminate parallax to be caused by the distance between the optical axes of the illuminating optical system and observing optical system. Moreover, in case of the second embodiment shown in FIG. 3, it is more preferable to arrange so that the focal point of the positive lens 13 comes onto the exit surface 12c of the prism 12, i.e., at a position near the exit of the viewing-direction changing attachment according to the present invention because it is then possible to make the size of the prism 12 smallest. Thus, it is possible to make the attachment compact and, at the same time, it is possible to illuminate a wide area and to substantially eliminate parallax as described in the above.

When the optical system according to the present invention is used, it is possible to use a forward-viewing type endoscope for the purpose of side viewing and, moreover, to attain favourable side-viewing observation free from flare and ghost as explained so far. Besides, as it is possible to attain uniform illumination for a wide area, it is also possible to observe the object with a wider field angle.

Though the above description is given referring to an optical system employing prisms, reflecting mirrors may be arranged at positions of the reflecting surfaces 11a and 12a instead of prisms. In that case, the optical system of viewing-direction changing attachment according to the present invention may be formed by arranging the reflecting mirrors, which correspond to the reflecting surfaces 11a and 12a, respectively at the pre-determined positions by using a suitable mount.

I claim:

1. An optical system of a viewing-direction changing attachment for endoscopes comprising a first prism having a reflecting surface for changing the observing direction and a second prism having a reflecting surface for changing the illuminating direction and arranged so that the reflecting surface of said second prism comes to a fore position compared with the reflecting surface of said first prism when said optical system of the viewing-direction changing attachment is attached to a distal end of an endoscope, said first and second prisms being arranged that the entrance surface of said first prism becomes substantially flush with the exit surface of said second prism, said optical system of viewing-direction changing attachment being arranged to change the observing direction by attaching it at the distal end of the endoscope.

2. An optical system of viewing-direction changing attachment for endoscopes according to claim 1 further comprising a positive lens arranged between said second prism and distal end face of the endoscope.

3. An optical system of viewing-direction changing attachment for endoscopes according to claim 2, in which said positive lens is arranged so that its focal point comes to a position near the exit of said optical system of viewing-direction changing attachment.

4. An optical system of viewing-direction changing attachment for endoscopes according to claim 1, in which said first and second prisms are arranged that the exit surface of said first prism and entrance surface of said second prism come to positions comparatively close to each other and that the exit surface of said first prism and entrance surface of said second prism come to positions near the end face of the endoscope when said attachment is attached at the distal end of the endoscope.

* * * * *